(12) United States Patent  
Damadian

(10) Patent No.: US 10,034,709 B1
(45) Date of Patent: Jul. 31, 2018

(54) FOCUSED RADIO FREQUENCY ABLATION

(71) Applicant: Fonar Corporation, Melville, NY (US)

(72) Inventor: Raymond V. Damadian, Woodbury, NY (US)

(73) Assignee: Fonar Corporation, Melville, NY (US)

(*) Notice: Subject to any disclaimer, the term of this patent is extended or adjusted under 35 U.S.C. 154(b) by 44 days.

(21) Appl. No.: 14/203,167

(22) Filed: Mar. 10, 2014

Related U.S. Application Data

(63) Continuation-in-part of application No. 13/073,271, filed on Mar. 28, 2011, now Pat. No. 8,934,990, which is a continuation of application No. 13/039,866, filed on Mar. 3, 2011.

(60) Provisional application No. 61/339,453, filed on Mar. 4, 2010, provisional application No. 61/775,615, filed on Mar. 10, 2013.

(51) Int. Cl.
   *A61F 7/00* (2006.01)
   *A61N 5/00* (2006.01)
   *A61B 18/18* (2006.01)

(52) U.S. Cl.
   CPC .................. *A61B 18/18* (2013.01)

(58) Field of Classification Search
   CPC .... A61K 41/0052; A61N 1/403; A61N 1/406; A61N 5/1001
   See application file for complete search history.

(56) References Cited

U.S. PATENT DOCUMENTS

| 4,230,129 | A |  | 10/1980 | LeVeen |
|---|---|---|---|---|
| 4,462,412 | A |  | 7/1984 | Turner |
| 5,097,844 | A |  | 3/1992 | Turner |
| 5,284,144 | A |  | 2/1994 | Delannoy et al. |
| 5,492,122 | A |  | 2/1996 | Button et al. |
| 6,023,166 | A |  | 2/2000 | Eydelman |
| 6,028,429 | A |  | 2/2000 | Green et al. |
| 6,107,974 | A |  | 8/2000 | Votruba et al. |
| 6,249,121 | B1 |  | 6/2001 | Boskamp et al. |
| 6,677,753 | B1 |  | 1/2004 | Danby et al. |
| 6,807,446 | B2 |  | 10/2004 | Fenn et al. |
| 7,123,010 | B2 |  | 10/2006 | Krockel |
| 7,466,130 | B1 |  | 12/2008 | Votruba et al. |
| 7,510,555 | B2 | * | 3/2009 | Kanzius ................. A61N 1/406 128/898 |
| 7,573,432 | B1 |  | 8/2009 | Eydelman et al. |
| 7,627,381 | B2 | * | 12/2009 | Kanzius ............. A61K 41/0052 607/101 |

(Continued)

*Primary Examiner* — Ronald Hupczey, Jr.

(74) *Attorney, Agent, or Firm* — Lerner, David, Littenberg, Krumholz & Mentlik, LLP

(57) ABSTRACT

This disclosure is directed to a method of applying spatially localized radio frequency ("RF") beam to a target location by placing RF resonant circuits at the target location. In a preferred embodiment, the target location is a portion of the anatomy of a subject, e.g., a tumor in a human body, and the RF resonant circuits are placed at the target location using a catheter or needle injection. The localized RF beam is provided is provided by a RF transmitter whose frequency is tuned to those of the RF resonant circuits. The RF transmitter may thus selectively supply concentrated thermal radiation capable of treating the target location without significantly heating (e.g., damaging due to high temperatures, or exposure to prolonged increased temperatures, etc.) areas proximate the target location (e.g., healthy tissue in other portions of the body.

20 Claims, 17 Drawing Sheets

(56) References Cited

U.S. PATENT DOCUMENTS

| | | |
|---|---|---|
| 7,701,209 B1 | 4/2010 | Green |
| 7,769,468 B2 | 8/2010 | Turner et al. |
| 8,055,326 B1 | 11/2011 | Dworkin et al. |
| 8,129,991 B2 | 3/2012 | Wahl et al. |
| 2007/0118193 A1 | 5/2007 | Turner et al. |
| 2007/0250139 A1* | 10/2007 | Kanzius ............... A61N 1/406 607/100 |
| 2009/0132015 A1 | 5/2009 | Miller et al. |
| 2010/0318162 A1 | 12/2010 | Rose |

* cited by examiner

FOCUSED RADIO FREQUENCY ABLATION

CROSS-REFERENCE TO RELATED APPLICATIONS

The present application claims the benefit of the filing date of U.S. Provisional Application No. 61/775,615, filed Mar. 10, 2013, entitled "Focused Radio Frequency Ablation," and is a continuation-in-part of U.S. application Ser. No. 13/073,271, entitled "Localized RF Heating," filed on Mar. 28, 2011, which is a continuation of U.S. application Ser. No. 13/039,866, filed on Mar. 3, 2011, and which also claims the benefit of the filing date of U.S. Provisional Application No. 61/339,453, filed Mar. 4, 2010. The disclosures of each of these applications are hereby incorporated herein by reference.

BACKGROUND

This disclosure relates to radio frequency ("RF") ablation system and methods, and more particularly to methods and systems of applying one or more spatially localized radio frequency ("RF") beams to a target location by placing RF resonant circuits at the target location.

RF ablation is a technique used to treat tumors in human subjects. In RF ablation, a needle attached to an RF source operating at about 350 to 500 kHz is inserted into a tumor. The source is used to heat up the tumor, e.g., around 50 to 60 degrees centigrade, causing destruction of the tumor. This heating is accomplished more from resistive heating rather than absorption of the RF energy by the tissue. The heating may cause damage to surrounding healthy tissue and minimizing this drawback is an important consideration in using RF ablation.

In that regard, other uses for RF heating include heating muscles or joints to decrease inflammation and increase blood flow, pain management, as well as certain sleeping disorders. RF ablation may also be used in the heart to destroy abnormal tissue or pathways that cause electrical activity of the heart to speed up or slow down. In these uses, as for the case of tumor treatment, minimizing or limiting the impact of heating on healthy surrounding tissue is desirable.

SUMMARY

The disclosure includes a method for radio frequency ablation, comprising transmitting radio frequency energy to one or more tuned radio frequency beads located at one or more portions of anatomy of a subject, each radio frequency bead being tuned to an independent frequency; and tuning a frequency of the transmitted energy to selectively concentrate the energy so that the portion of the anatomy associated with a particular bead is heated.

In another aspect, the method further preferably comprises selectively tuning the frequency of the transmitted radio frequency energy so that each of the one or more tuned radio frequency beads is selectively heated.

The method may also comprise eliciting magnetic resonance image signals from at least one of the portions of the anatomy at which the one or more beads are located.

In yet another aspect the method may further comprise providing an magnetic resonance image of at least one of the portions of the anatomy at which the one or more beads are located using the elicited magnetic resonance image signals.

Further still, the method may comprise tuning the frequency of the transmitted radio frequency energy so that each of the one or more tuned radio frequency beads is concurrently heated.

The method may further also comprise simultaneously monitoring each portion of the anatomy at which a tuned radio frequency bead is located using magnetic resonance imaging techniques.

The method may also comprise concurrently monitoring each portion of the anatomy at which a tuned radio frequency bead is located using magnetic resonance imaging techniques and repeating the transmitting and monitoring steps until the portion of the anatomy associated with a particular bead is determined to contain dead tissue.

The disclosure also includes a radio frequency ablation system. The system comprises a radio frequency transmitter; one or more radio frequency beads, each bead being tuned to a different radio frequency, and wherein at least one of the one or more radio frequency beads is placed in a first portion of an anatomy and the radio frequency transmitter transmits energy at the frequency that the at least one of the one or more radio frequency beads is tuned to selectively concentrate the energy in an area associated with the first portion of the anatomy.

In accordance with this aspect of the present invention, more than one of the one or more radio frequency beads are placed at different portions of the anatomy, each of the more than one radio frequency beads is tuned to a different frequency.

In accordance with this aspect of the present invention, the radio frequency transmitter transmits energy at each of the different frequencies that the more than one radio frequency beads are tuned so as to selectively concentrate the energy at the different portions of the anatomy that the more than beads are placed.

Further, the transmitter is selectively tuned to transmit energy at a frequency that only one of the more than one radio frequency beads is tuned.

Further still, the transmitter is selectively tuned to concurrently transmit energy at each of the frequencies that the more than one radio frequency beads are tuned.

In addition, the system may further comprise magnetic resonance signals that are used to visualize the first portion of anatomy at which the bead is placed.

DETAILED DESCRIPTION

In an aspect of this invention, RF energy is desirably applied externally to the body from several sources. Each source will be of sufficiently low power as to not cause any ill effects to the individual under treatment, including damaging healthy tissue. The energy will be at a level that will heat the tissue at a point that these multiple sources are aimed (the focus location). For example, if a tumor is present, the RF energy desirably heats the tumor causing its death.

Because of possible interference of multiple RF sources being turned on at once, one alternative embodiment would be to pulse the different sources sequentially so that no two are on simultaneously. In a modification of this embodiment, each RF source could be tuned to a slightly different frequency, thus avoiding interference. Alternatively, the RF source could be moved in such a manner that the focused point is always hit and the surrounding tissue moves in and out of the RF field.

This internal heating of the tumor can be followed in an MRI system. Magnetic resonance imaging is well suited to follow the temperature rise deep in the body and determine when target temperatures are reached. In one embodiment of the invention, the apparatus for heating the tumor would be placed in the MRI system.

The choice of frequencies that would be used would depend on several issues such as the RF absorption of the targeted tissue, the mechanism of the cells destruction, and absorption of tissue surrounding the focus location, and scattering of the RF by bone and other organ interfaces.

The choice of the frequencies could also determine the structure and type of RF source used in the invention. In general, all the RF sources can consist of several nested coils. With the inner coils 120 and 130 generating the main field and outer coils 110 and 140 limiting and focusing the RF beam. (See FIGS. 1 and 2.) The Focusing Coils 110 and 140 generate an RF field that is 180 degrees out of phase from the central main field. The beam would be designed to be as narrow as possible. The length of the beam would only have to be about 6 inches or half the reach across the human body.

Multiple sources of focused RF could then be aimed at a single point within the body, or a single source could be moved to avoid surface heating but still aimed at a single point within the body. Either approach would still be capable of heating the tumor deep within the body, while keeping the surface heating to a minimum.

Figure 3:
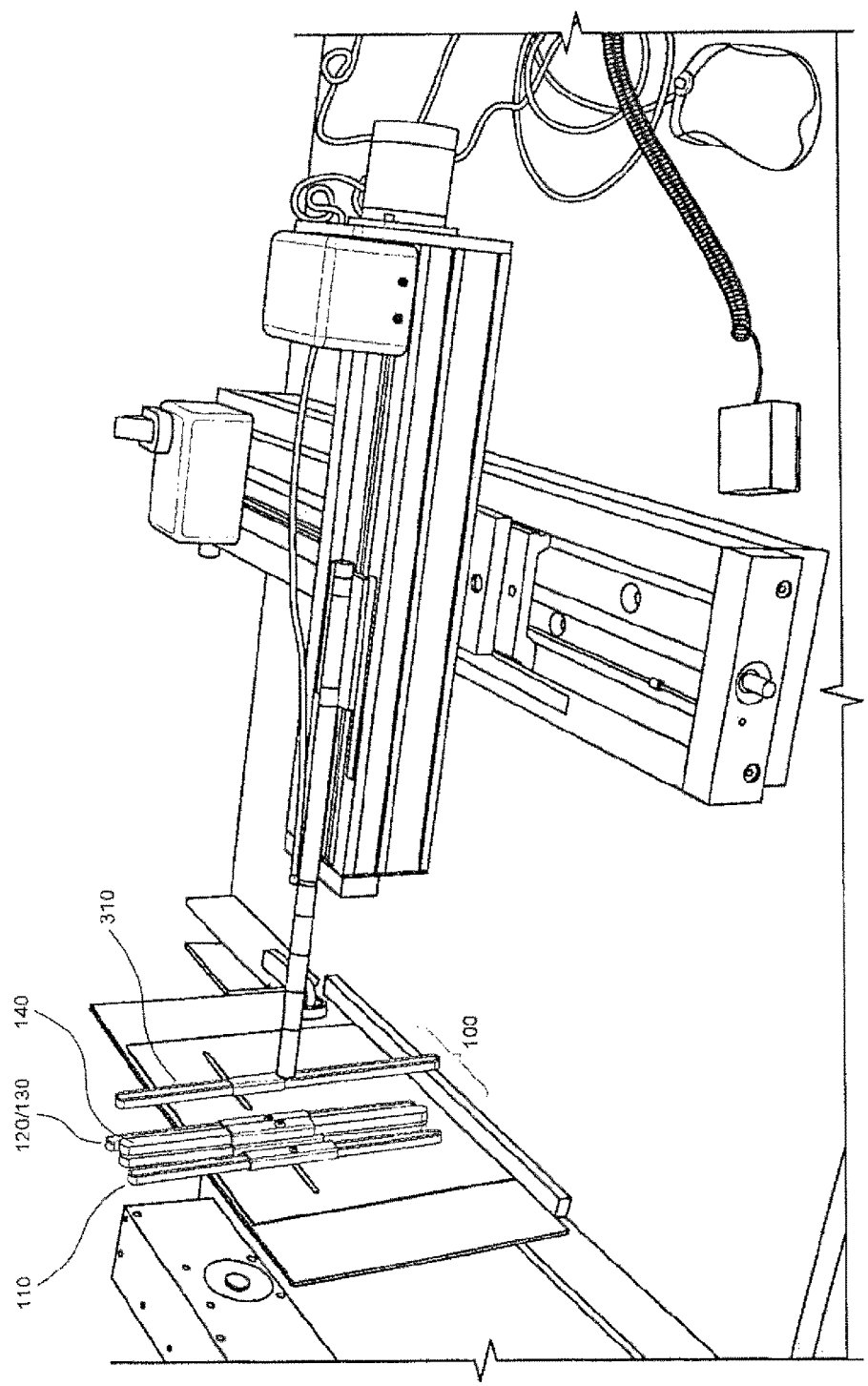
FIG. 3 shows an example experimental setup in accordance with aspects of the invention.
Figure 4:
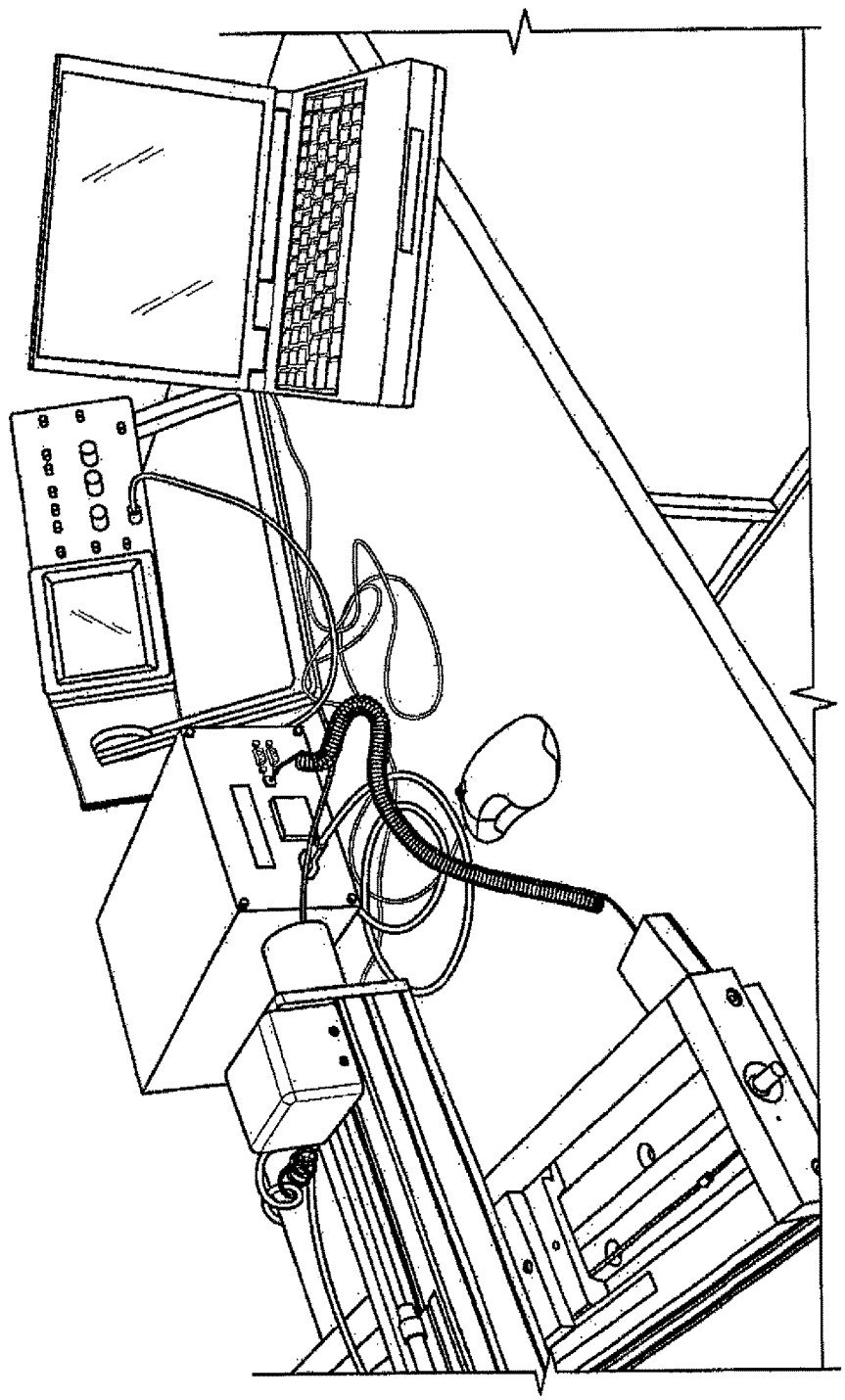
FIG. 4 shows another example experimental setup in accordance with aspects of the invention.
Figure 5:
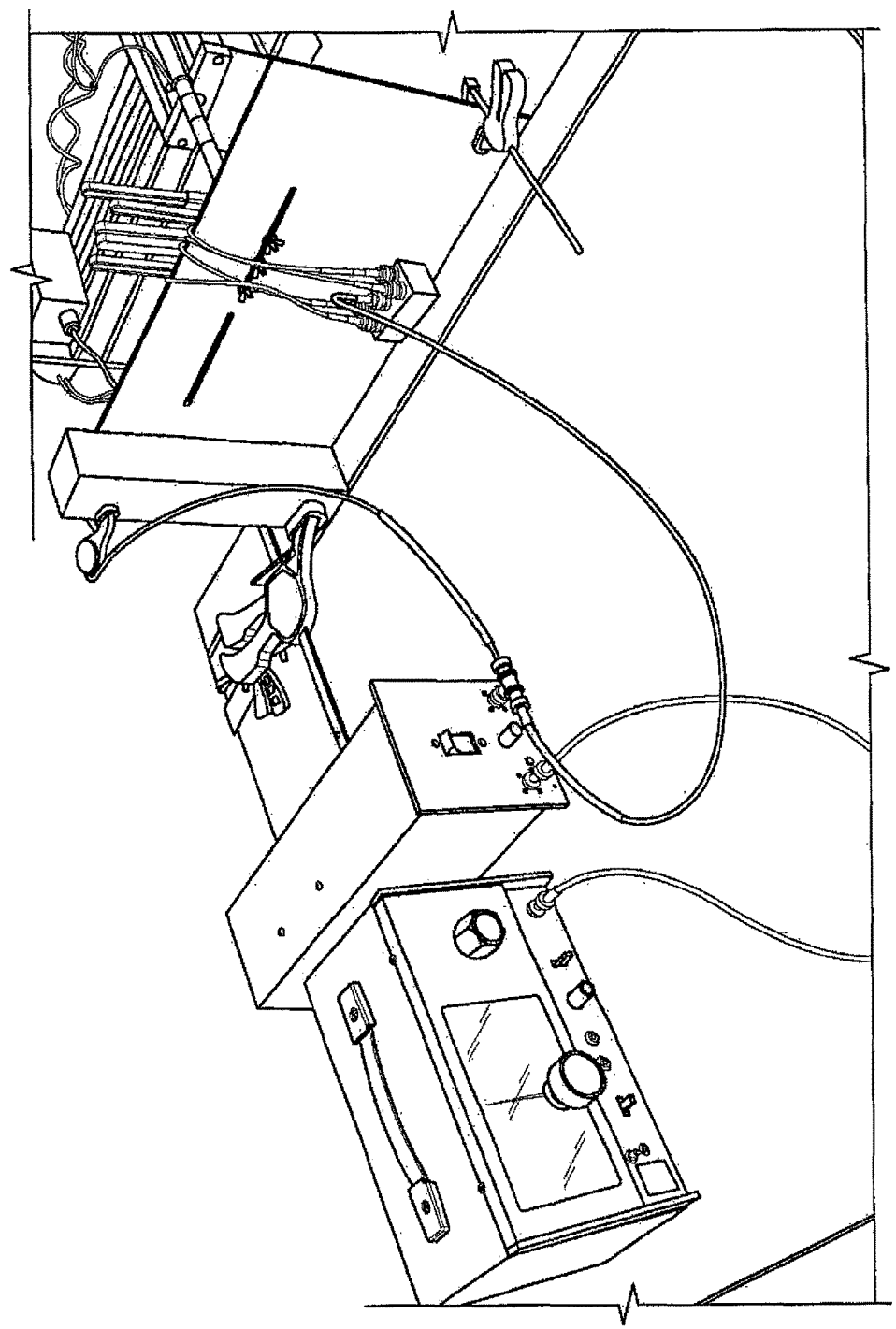
FIG. 5 shows a further example experimental setup in accordance with aspects of the invention.
Figure 6:
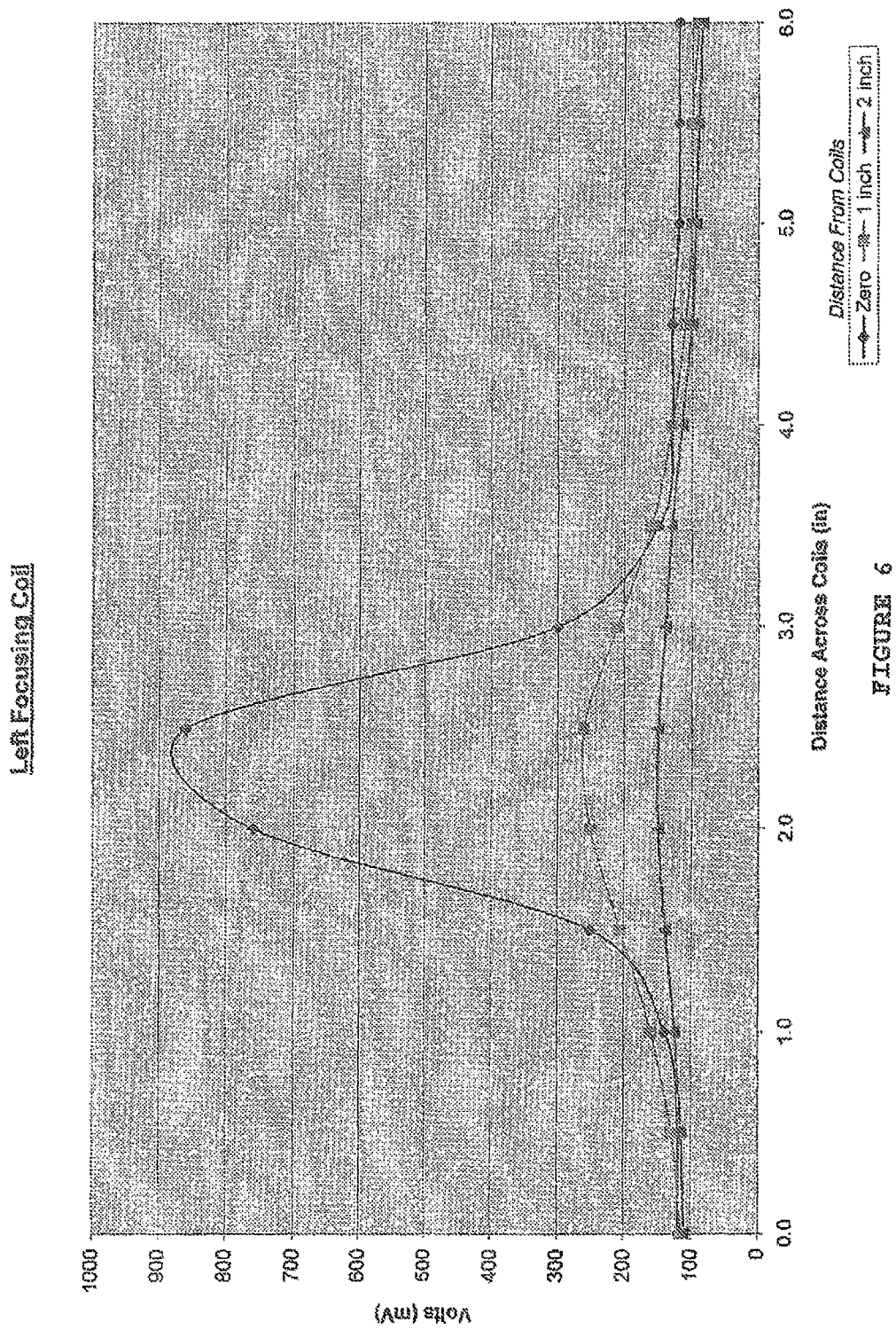
FIG. 6 shows an example RF energy plot generated in accordance with aspects of the invention.

In the first approach to focused RF ablation (FIG. 1) two central coils 120 and 130 are used. They are flanked by two focusing coils 110 and 140 on either side. FIG. 3 shows the experimental setup 300 used to map the RF fields. At the end of the wooden dowel 305 is the sensor coil 310 that can be passed across the array 100 of RF coils 110-140 at different distances. The first graph labeled "Left Focusing Coil" (FIG. 6) shows the amount of RF energy detected on the oscilloscope (FIG. 4) when only the left focusing coil 110 is energized. The three plots show the sensor being passed at different distance from the coil array 100.

Figure 7:
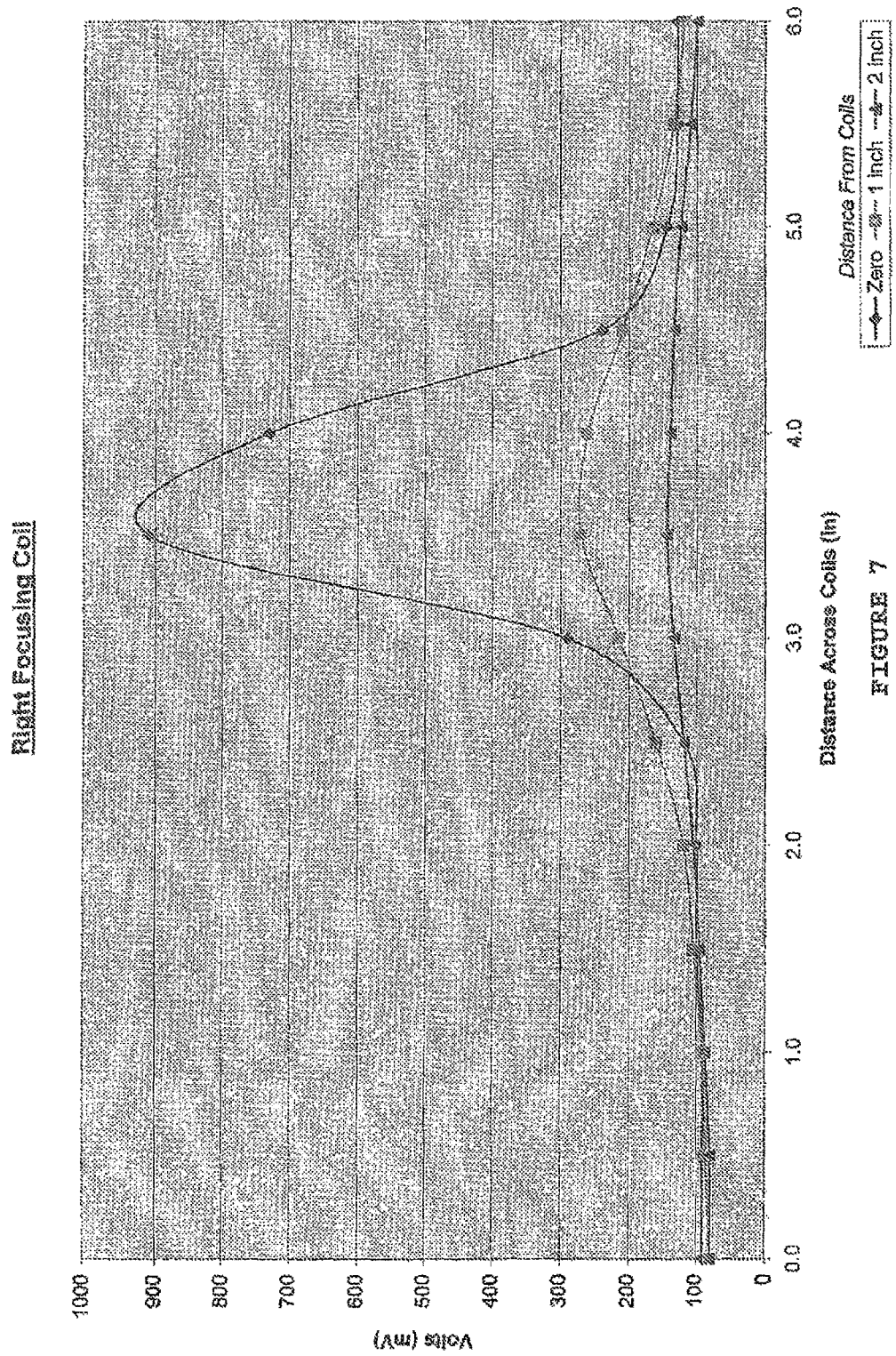
FIG. 7 shows another example RF energy plot generated in accordance with aspects of the invention.
Figure 8:
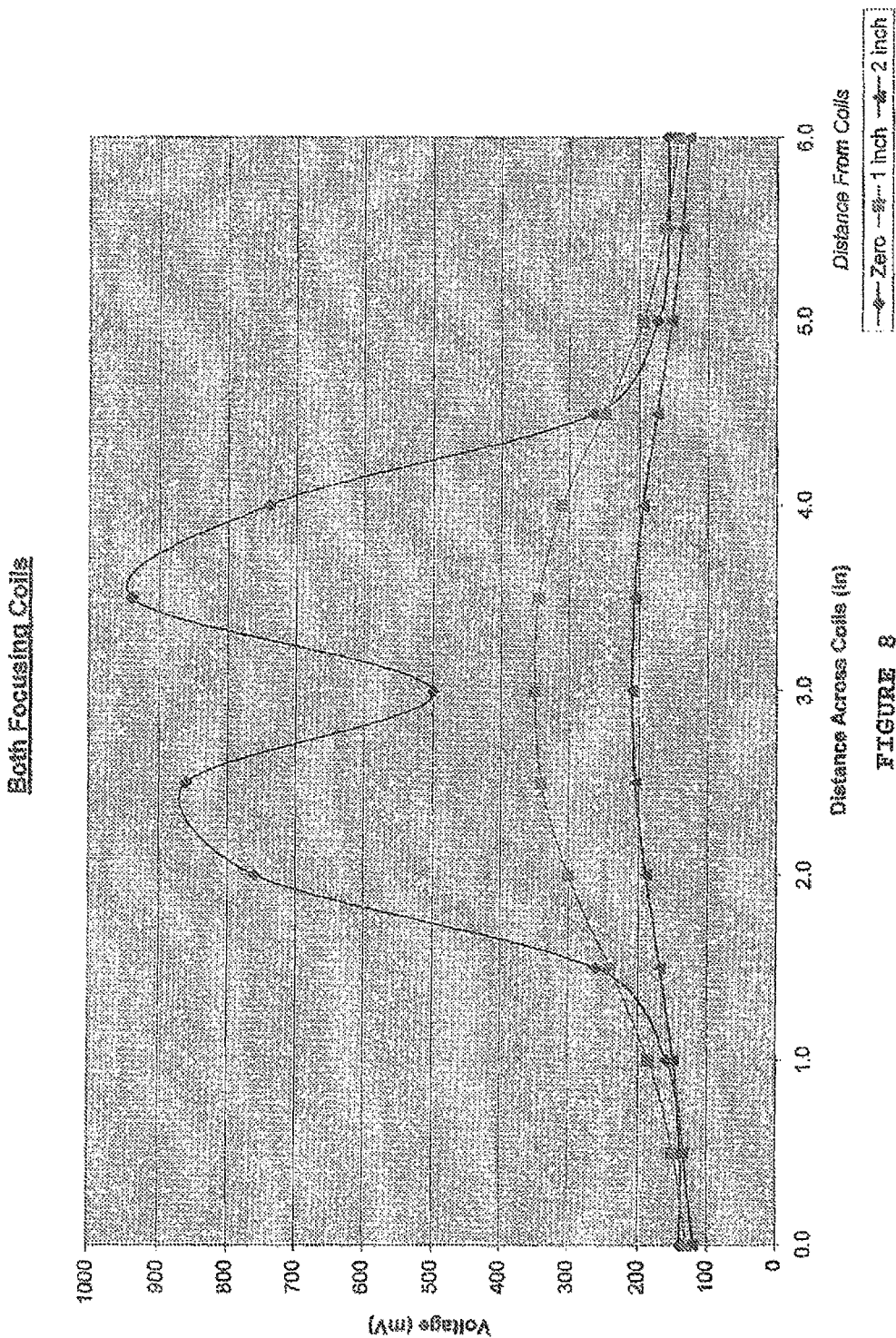
FIG. 8 shows a further example RF energy plot generated in accordance with aspects of the invention.

The next graph labeled "Right Focusing Coil" (FIG. 7) is similar to the previous plots only the right coil 140 is energized. Similarly with the graph labeled "Both Focusing Coils" (FIG. 8) the plots show energy distributions from both Focusing Coils 110 and 140.

Figure 1:
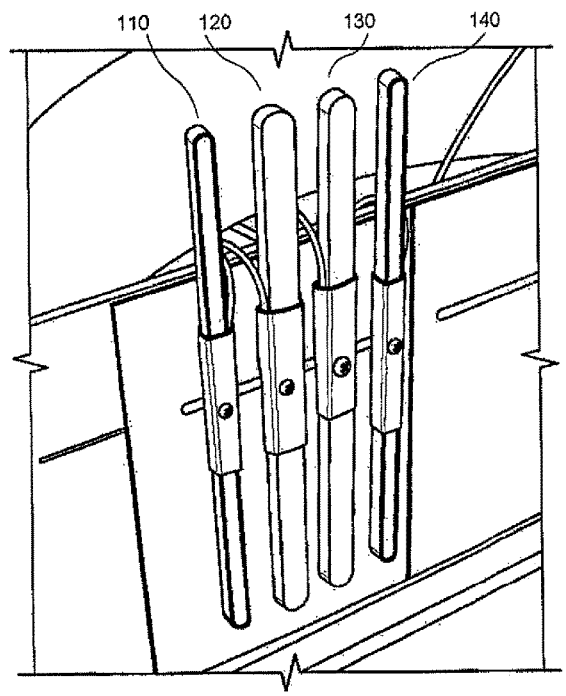
FIG. 1 shows an example apparatus in accordance with aspects of the invention.
Figure 9:
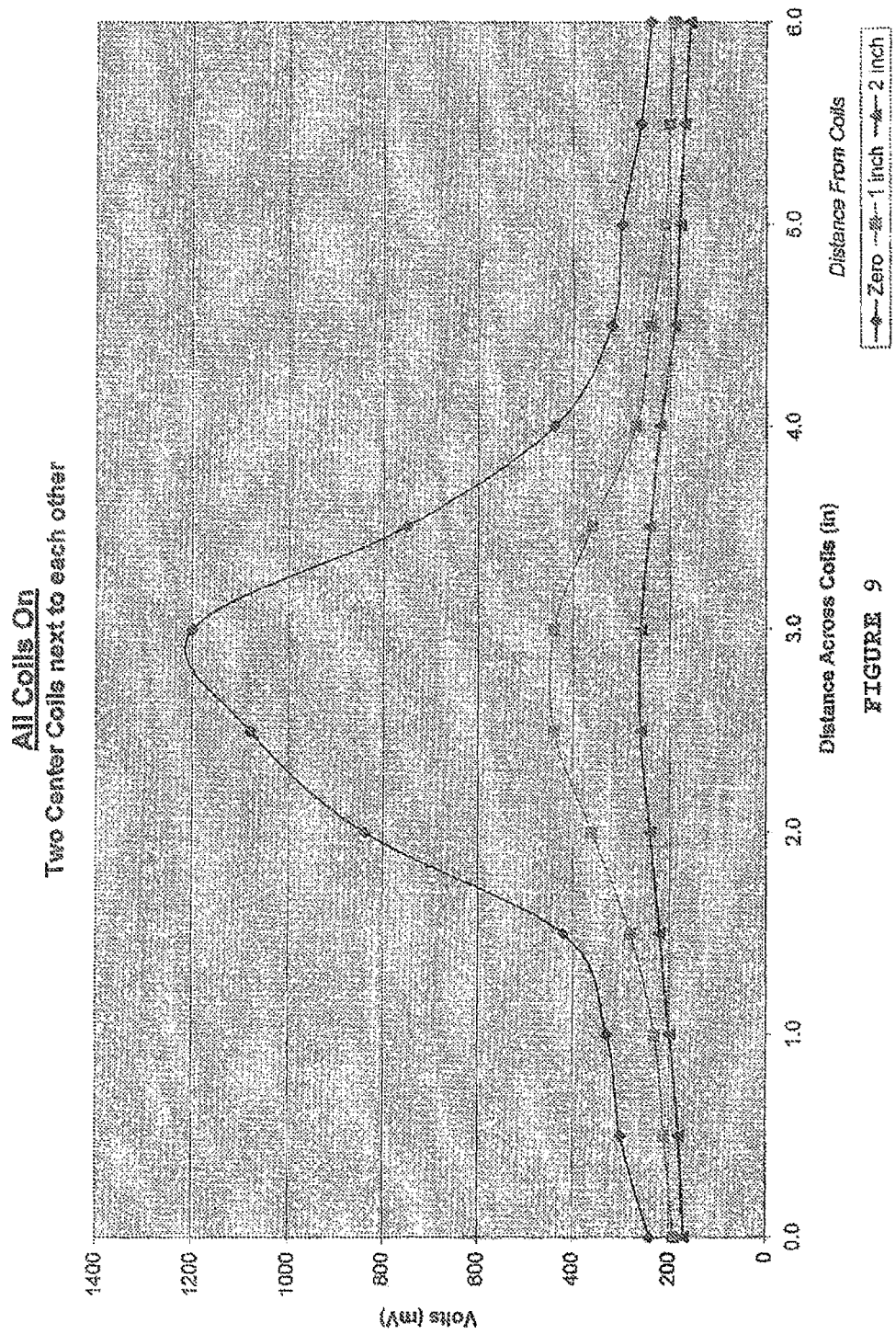
FIG. 9 shows yet another example RF energy plot generated in accordance with aspects of the invention.
Figure 10:
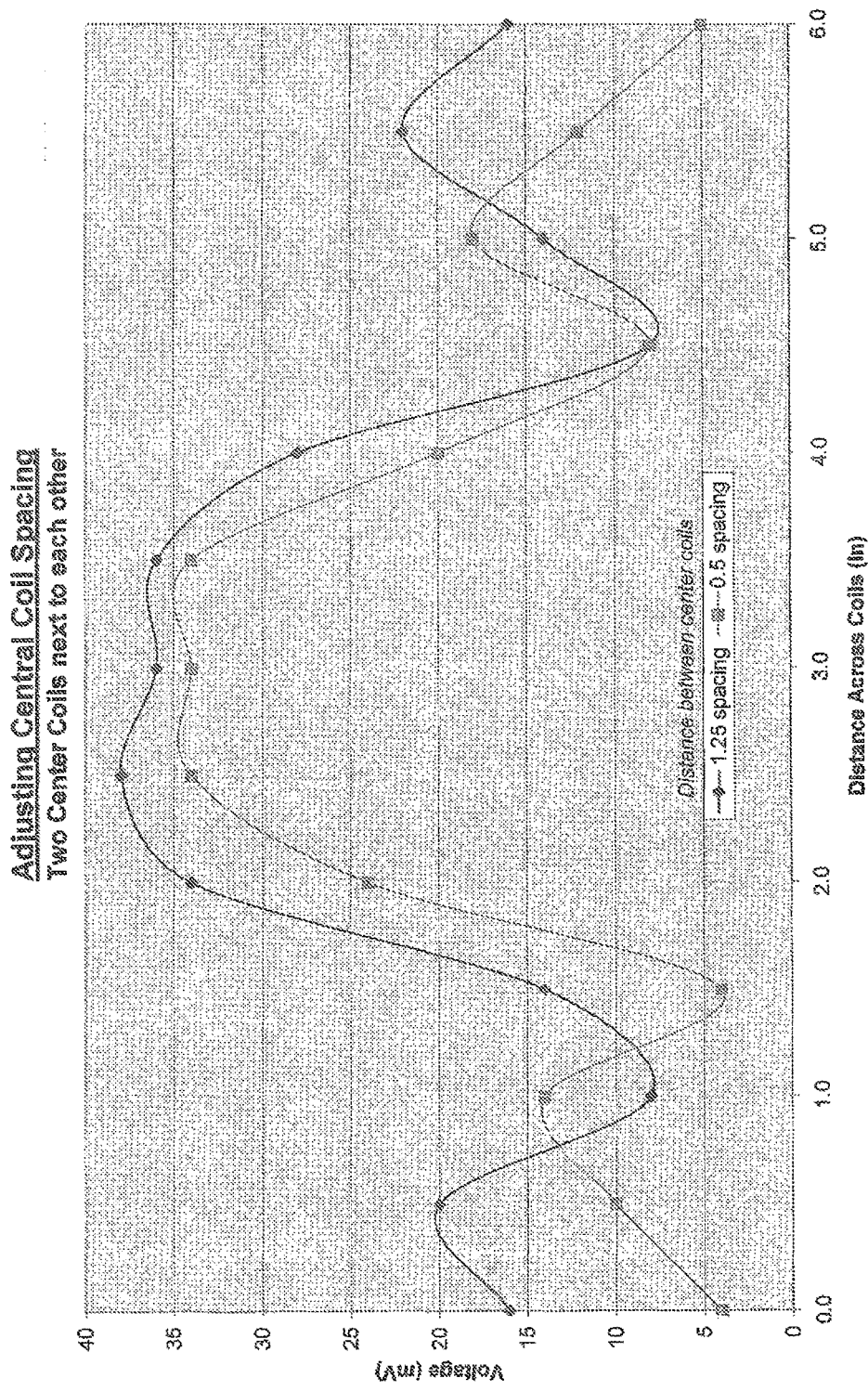
FIG. 10 shows another example RF energy plot generated in accordance with aspects of the invention.

The graph labeled "All Coils On" (FIG. 9) shows the RF field produced in an array as in FIG. 1 with two central coils 120 and 130 are next to each other. The effect of adjusting the distance between the two central coils 120 and 130 is illustrated in the graph labeled "Adjusting Central Coil Spacing" (FIG. 10).

Figure 2:
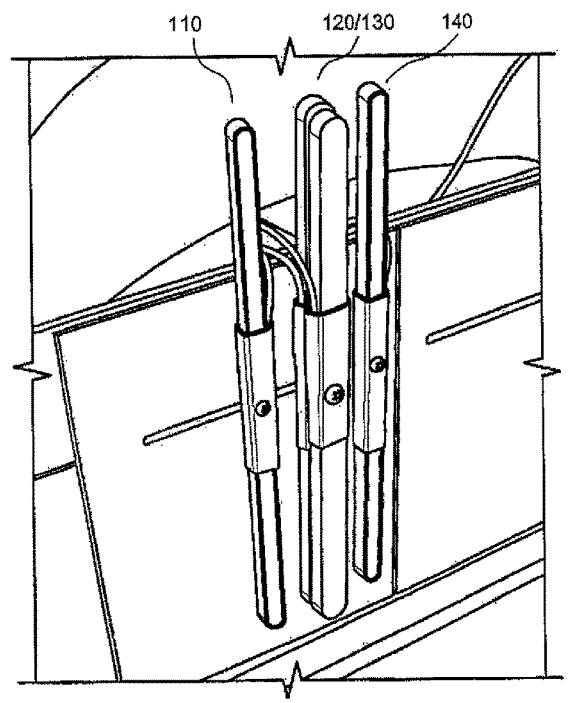
FIG. 2 shows another example apparatus in accordance with aspects of the invention.
Figure 11:
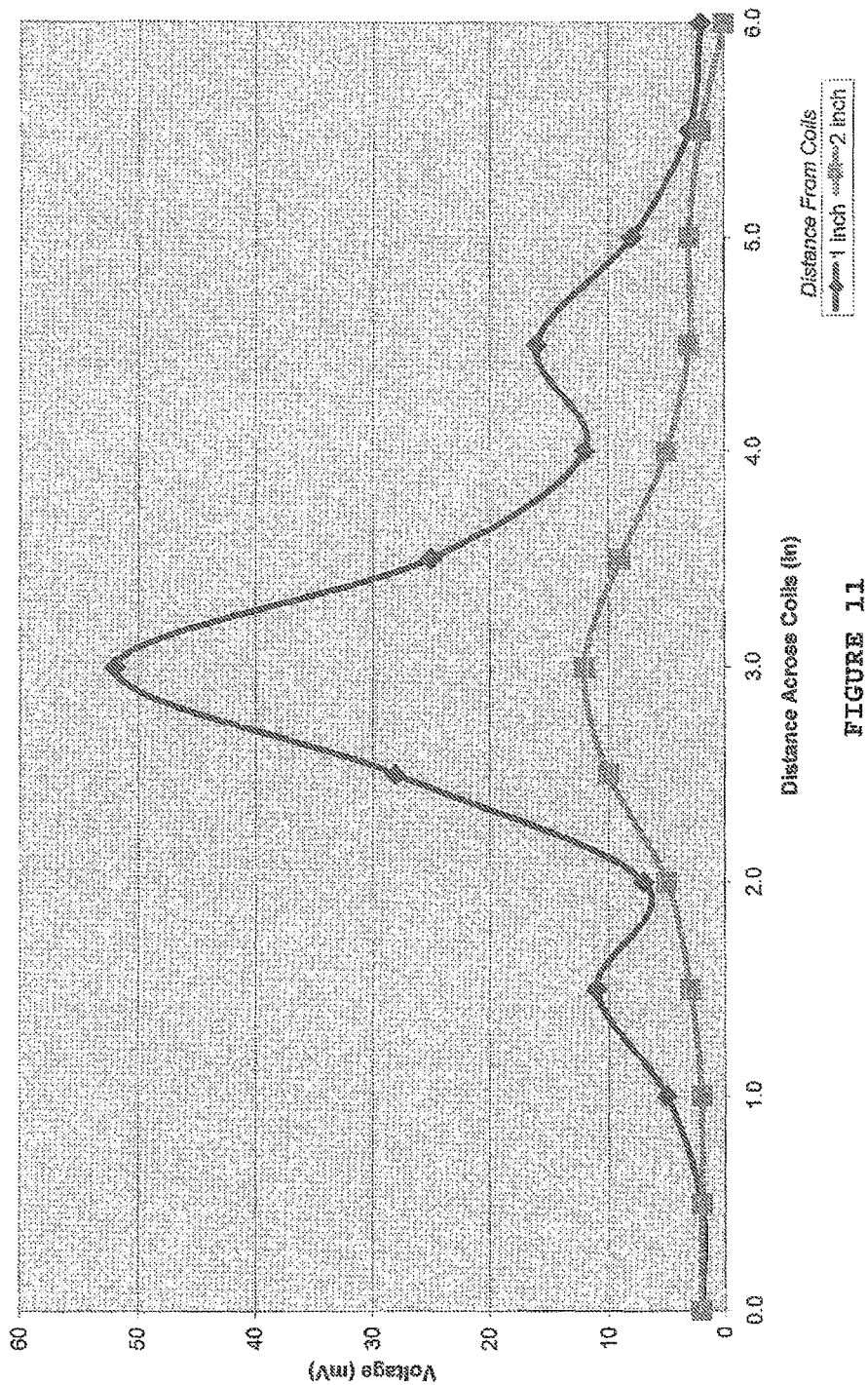
FIG. 11 a further example RF energy plot generated in accordance with aspects of the invention.

To try to increase the amount of RF Focusing, the Central Coils 120 and 130 were placed on top of each other (FIG. 2). This increased the RF field generated by the central main coil 120/130 and put double the number of ampere tunes in the main coil 120/130 as the side Focusing Coils 110 and 140. The result is a sharper focused RF beam as seen in the graph labeled "Single Center Coil" (FIG. 11).

Figure 12:
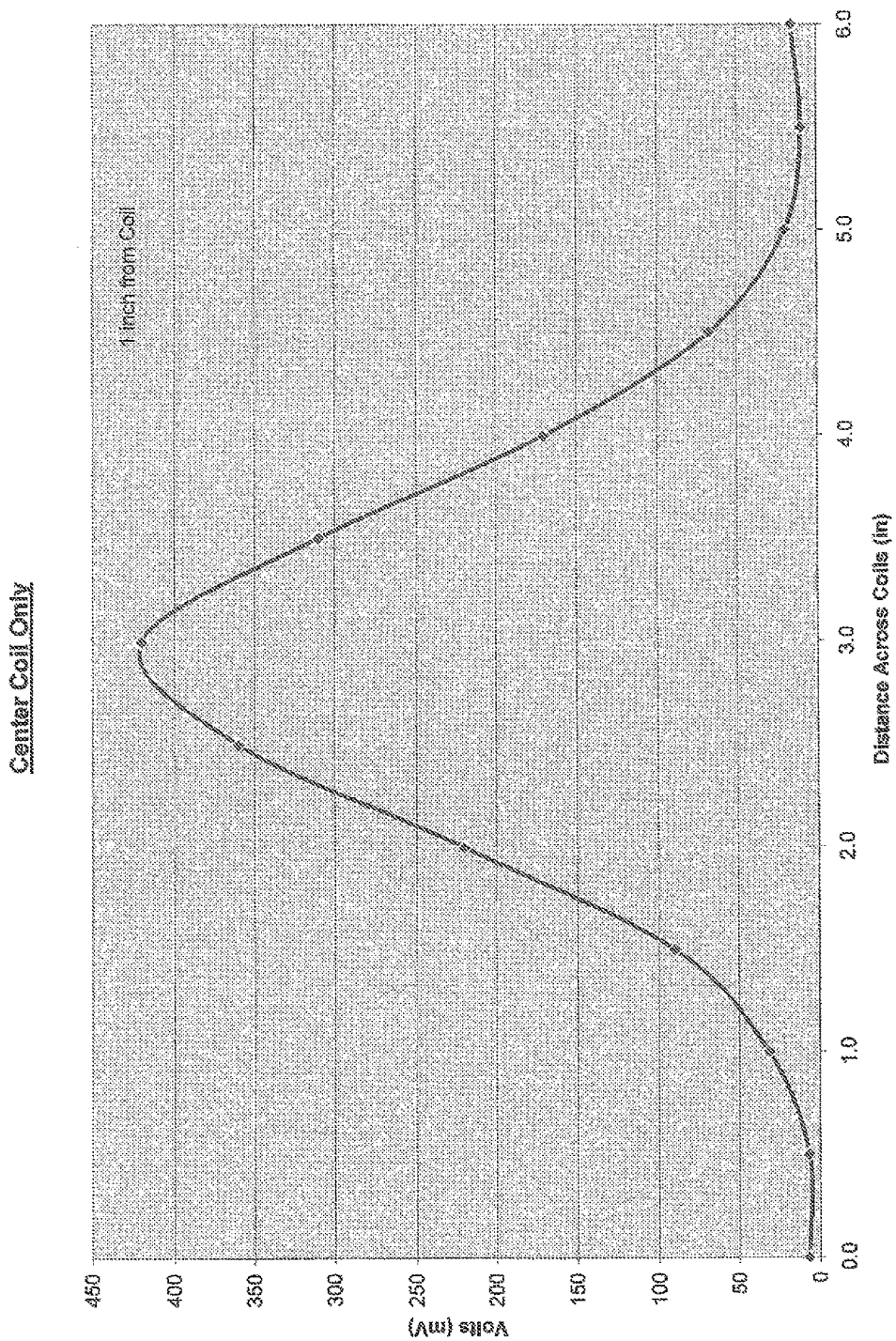
FIG. 12 shows yet another example RF energy plot generated in accordance with aspects of the invention.

As a point of reference the graph labeled "Center Coil Only" (FIG. 12) has only the main coil 120/130 on but without the focusing coils 110 and 140 being energized. The plot is done at the same 1 inch distance from the coils as was the previous graphs, "Single Center Coil" (FIG. 11). Without the focus coils 110 and 140, the coil profile is as expected, covering a range from 1 inch to 5 inches on the x-axis. When the focusing coils 110 and 140 are on, the range of the profile is from 2 inches to 4 inches. The difference in voltage measured is a function of power distribution, i.e., power going to one coil as compared to four coils.

Figure 13:
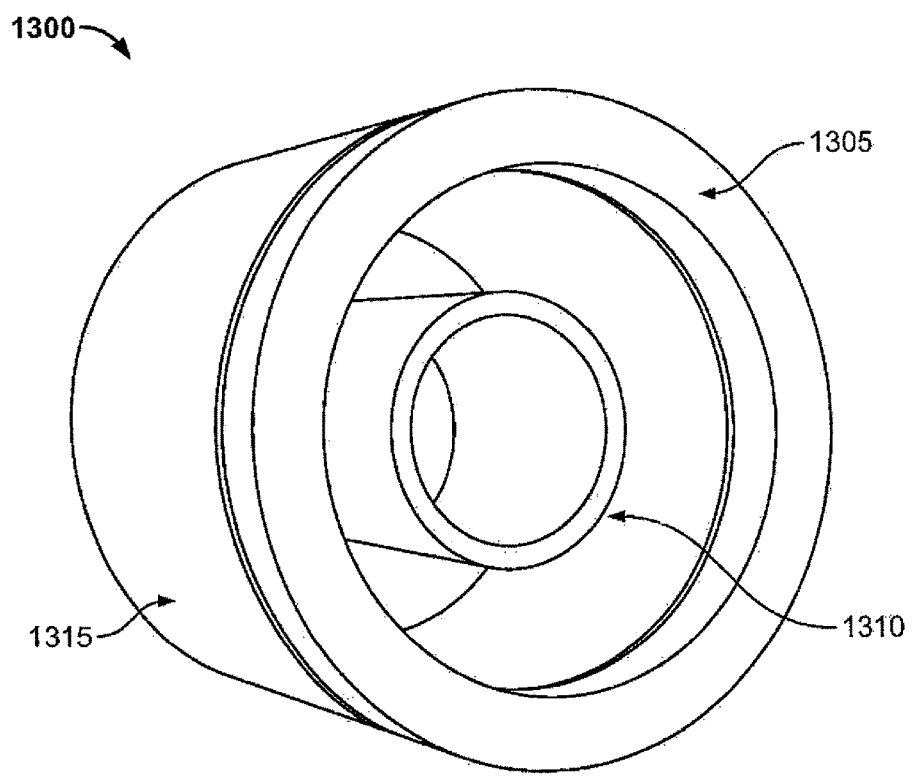
FIG. 13 shows an example apparatus in accordance with aspects of the invention.

A refinement 1300 of the previously described RF coil array is shown in the illustration of FIG. 13. The central (Main Coil) coil 1310 is housed in an Aluminum (Copper or any other highly conducive metal would do) housing 1315. This limits the RF fringe field and helps direct the field in the desired direction. The geometry of the housing 1315 could be simply a metal can or more sophisticated as parabolic or elliptical.

A Focusing Coil 1305 is placed at the mouth of the metal housing 1315 and carried current 180 degrees out of phase with the main coil. The amount of current in the Focusing Coil 1305 relative to the Main Coil 1310 will determine the nature and shape of the RF Beam. In one embodiment, two of these nested coils are placed on the same axis on either side of the patient. This permits them to work together to produce a better controlled RF Beam.

It is known that malignant tissue can be destroyed by temperatures which a healthy tissue is still able to tolerate without being damaged.

The concentration of thermal energy can be accomplished by a special arrangement of an array 1400 of RF coils surrounding the body and driven by a special power switching time sequence.

Many attempts have been made to destroy tumors by electromagnetic field at microwave frequencies in the past.

The problem with this approach is that the near-field regime does not hold well resulting in contamination of the sample by the electric component of the field. As a result, the localization of thermal energy was unpredictable and heating occurred at the wrong places in the body. In modern times, these problems have been solved by using low-frequency RF. In this case, it is feasible to work in pure quasi-stationary mode with RF magnetic fields. There are, however, still difficulties related to having a strong field close to the RF applicators resulting in overheating of the healthy tissue in the surface areas of the body. Progress has been made in U.S. Pat. No. 4,230,129, which discloses operating at frequencies of 13.56 MHz. In the '129 patent, the undesirable superficial increase in ambient temperature, which would ultimately prevent the device from delivering the desired temperature to the tumor inside the body is addressed. Two RF coils are mechanically moved circumferentially around the body while maintaining the targeted area in focus.

In one embodiment of the present invention presented herein, the mechanical motion of two opposite RF coils is replaced by a stationary multiplicity (array) of RF coils and by a special time on-and-off power switching sequence among the said coils so as not to affect the surrounding tissue adversely.

Figure 14:
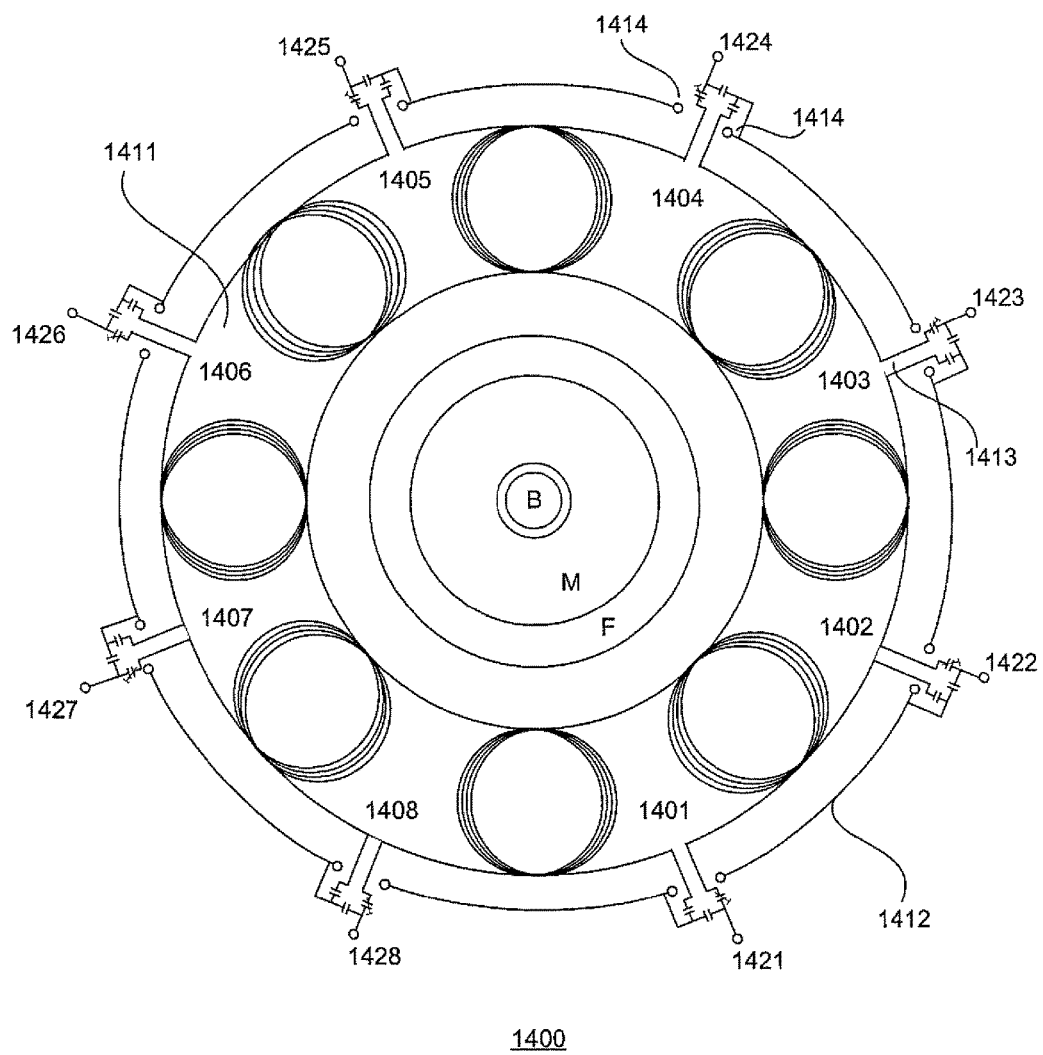
FIG. 14 shows another example apparatus in accordance with aspects of the invention.
Figure 15:
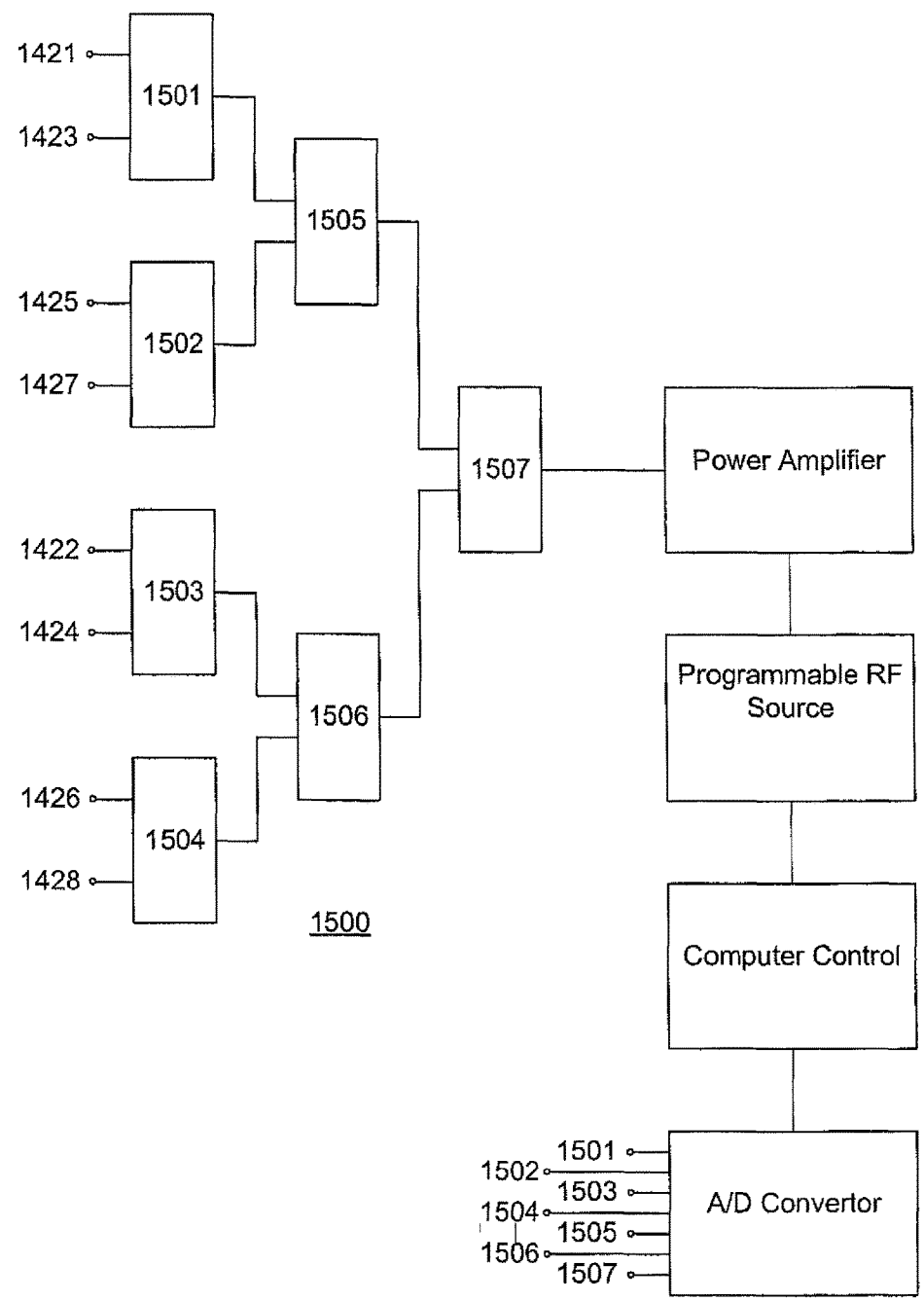
FIG. 15 shows an example RF power switching circuit and an example timing sequence in accordance with aspects of the invention.
Figure 16:
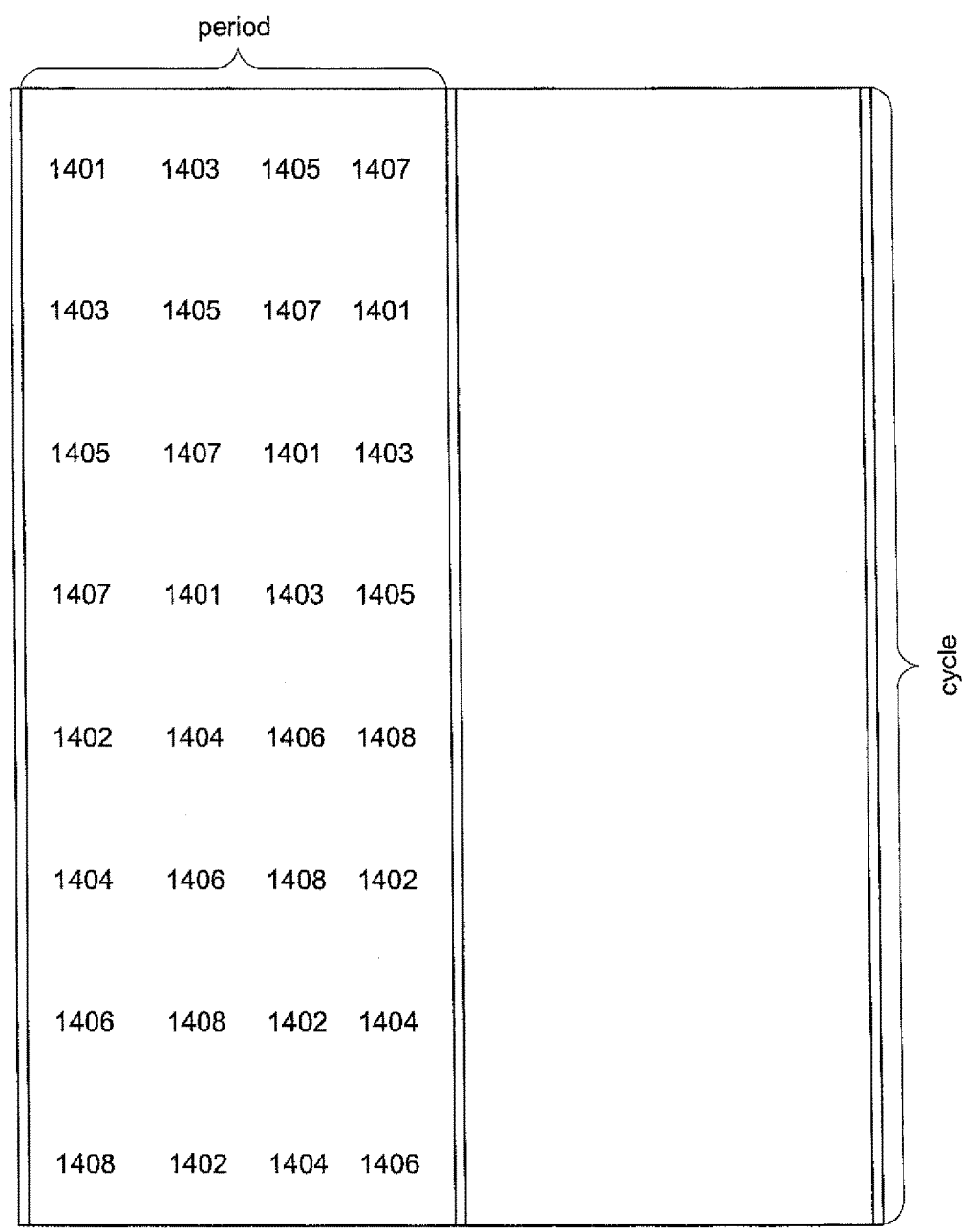
FIG. 16 shows an example of possible time sequence for switching the RF transmitters in accordance with aspects of the present invention.

In one embodiment, shown schematically in FIG. 14 a plastic cylindrical surface 1411, preferably 20" in diameter and 10" high, carries light circular overlapped RF rings. (For visualization, rings 1401-1408 are not shown in correct perspective in the diagram.) The assembly of eight RF coils 1401-1408 is surrounded concentrically by a RF mirror. The mirror is a cylindrical surface 1412, preferably 30" in diameter and 16" high, made from solid copper sheet or from a thin copper foil attached to a plastic cylindrical carrier. In this conductive cylinder there are eight holes 1413 for the RF input leads 1421-1428 to the RF coils 1401-1408. These holes 1413 have rounding inserts 1414 to prevent arcing discharges at high power levels. The RF coils 1401-1408 are matched to 50Ω when the whole assembly is loaded by a typical body or by a phantom with equivalent loading characteristics. While the RF coils are geometrically decoupled to diminish a cross talk among them, it is desirable to operate them at different resonant frequencies to further increase their electrical independence. The preferred set of frequencies are: 13.6, 13.8, 14.0, 14.2, 14.4, 14.6, 14.8 and 15.0 MHz. The input leads 1421-1428, with matching and tuning circuits are connected to an aggregate 1500 of seven RF power switches 1501-1507 shown in FIG. 15. The purpose of the switches 1501-1507 is to enable time sequencing of RF power in the RF coils. A chosen time sequence then provides a relaxation time for the surface areas of the body to cool down before the next heat RF pulse arrives. The duration of RF pulses could be one second, for example. As embodiment sequence shown in a form of a table 1600 in FIG. 16 has a power ON/power OFF ratio of 1:7 and 1:11. The adjacent coils can be energized at a ratio of 1:4, as is also shown in Table 1600.

For the best mode for carrying out or practicing this aspect of the invention, the following conditions should be addressed in the design of the device:

The RF field should be well separated into two components: the magnetic field generated by RF current in the coils and the electric field generated by the applied RF electromotoric force (voltage) inside the turning and matching capacities.

The coils should be well electrically separated to avoid cross-talk among them.

The ratio of power $P_L$ when the patient or phantom is loaded in the device to power $P_E$ when the device is empty, that is $\Gamma = P_L/P_E$, should be a big number. That means that the Q-value of individual coils should be high.

The distribution of thermal energy across the active volume inside of the device and the corresponding distribution of temperatures should be known for the device empty and the device loaded by a phantom. That could be accomplished by calorimetric methods, preferably by a lattice of liquid alcohol thermometric immersed in small test tubes filled with a conductive electrolyte.

Instead of simple rings, more complex rings can be used to increase the field penetration along the coil axis. Namely, let a ring with radius A has n turns and let there be second ring with radius B with m turns, located concentrically in the same plane and connected in series with the first ring and wound in opposite direction with respect to the first ring. let, further, the ratio A:B be equal to n:m where n and m are integers and n>m. Then the field along the x axis is $$H(x) = \frac{\mu_o I}{4\pi} \left( \frac{nA^2}{(A^2+x^2)^{3/2}} - \frac{m\left(\frac{m}{n}\right)^2 A^2}{\left[\left(\frac{m}{n}A\right)^2 + x^2\right]^{3/2}} \right)$$

that is H(0)=0. The maximum field is then found from $$\frac{dH(x)}{dx} = 0$$

and it is seen to be at $$x = \pm A * \left(\frac{m}{n}\right)^{3/5} * \sqrt{\frac{1-\left(\frac{m}{n}\right)^{4/5}}{1-\left(\frac{m}{n}\right)^{6/5}}} \;;$$

n>m

Figure 17:
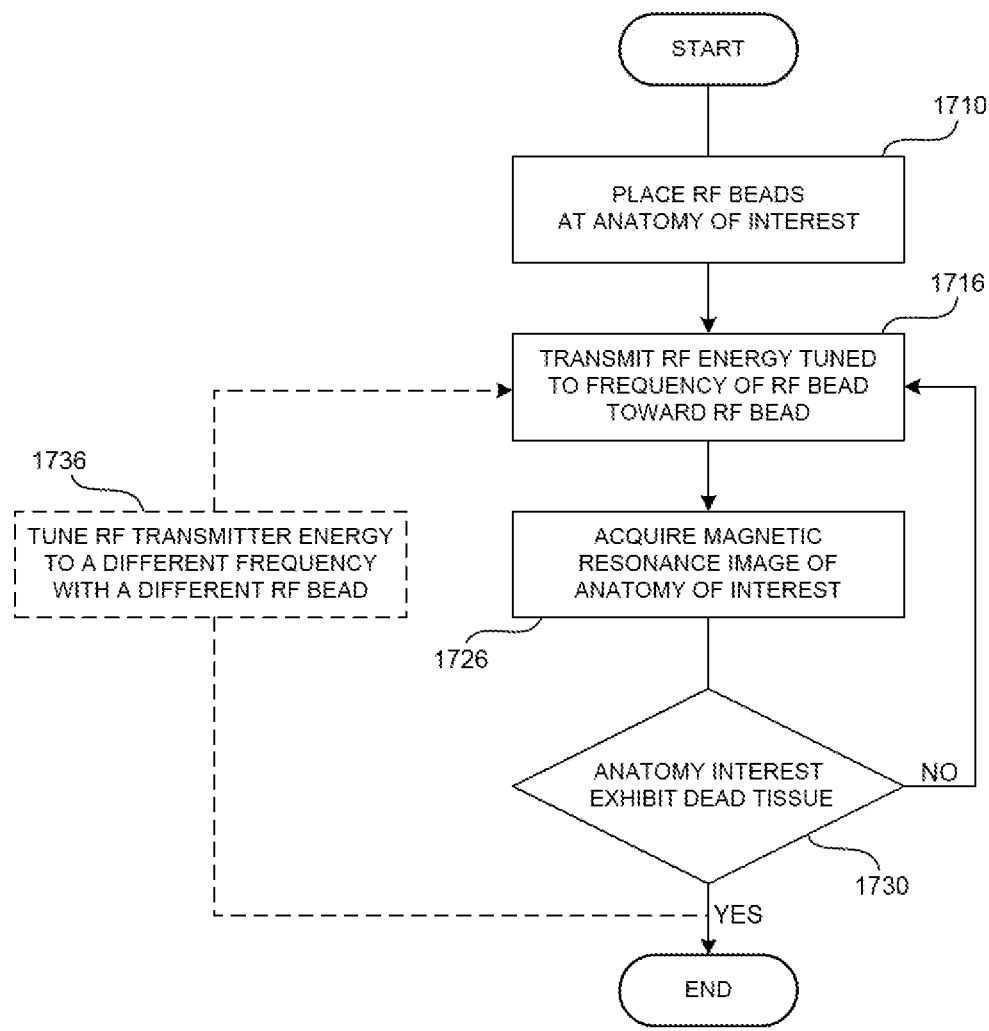
FIG. 17 illustrates a method in accordance with aspects of the present invention.

Turning now to FIG. 17, there is shown a method in accordance with a further aspect of the present invention. In accordance with the method, radio frequency ("RF") beads are placed at a location of interest within an object, block 1710. The object may comprise a human subject or tissue within a human subject, animal, etc. In addition, though the method is described as including placement of the beads as the first step, it is not necessarily the first step in the method. Rather, the method may also commence with the next block 1716, but after the beads have been located at a desired location.

With regard to locating the RF beads at the desired location, that may be accomplished by injection or microcharacterization by feeding arteriole tiny RF beads. In a preferred embodiment, the RF beads are placed into a tumor. Each RF bead may include a uniquely tuned RF circuit so that each bead is located at a different site within the tumor and thus uniquely identifies that site. For example, visualize a liver with five metastases located in five different liver segments. The RF beads are then delivered, either through needle injection or arterial catheterization, to the tumor sites such that each site receives a bead tuned to a different RF frequency. Thus, in this example, five beads each tuned to a different frequency would be implanted at each of the five hepatic tumor lesions.

Next, the spatially located RF beam described above in relation to FIGS. 1-16, would then be used to direct RF energy tuned to the frequency of the RF beads, block 1716. The RF transmitter would then transmit an RF beam that selectively concentrates its energy in the tumor that contains the circuit tuned to the RF transmitter's frequency.

In the case where one or more uniquely tuned RF beads are implanted, e.g., continuing the example above with the five uniquely RF beads, the RF energy may be tuned to target each of the five metastases in the liver. In this example, the transmitter may be tuned to deliver energy to each RF bead, one RF bead at a time. As indicated at block 1726, as the RF beads are energized the response of the tumor to heating may be monitored using an Magnetic Resonance Imaging ("MRI") apparatus. In accordance with this aspect of the present invention, the apparatus may comprise an UPRIGHT® MRI system, various versions of which are sold by Fonar Corporation, the assignee of the present application. The period and intensity of the radio frequency energy delivered to a site may be varied under MRI monitoring to optimize eradication of the lesion.

In that regard, once the tumor or anatomy of interest associated with a particular RF bead has been determined to be eradicated or comprises dead tissue, the process may end as shown at block 1730. Alternatively, if it is determined that additional treatment is needed, the process may return to block 1716 so that additional treatment can be performed as described above.

Alternatively, once it is determined at block 1730 that the anatomy of interest is sufficiently treated, the process may continue at block 1736 by tuning the transmitter to a different frequency. For example, the transmitter may be tuned to a second frequency, e.g., Frequency 2, and the MRI guided treatment process of blocks 1716 and 1726 repeated so that a tumor at a second site, e.g., tumor #2, can be destroyed. The process may thus be repeated step by step until all sites or targeted tumor lesions are destroyed as established by the concurrent MR imaging system.

In another embodiment, the RF transmitter may operated such that all RF beads are turned on concurrently. This may be accomplished by implanting multiple RF beads all tuned to the same frequency or by having the RF energy transmitted over a large enough band to energize each uniquely tuned RF bead. In this way, the response at all the monitored sites may done simultaneously by the MRI apparatus whereby any of the visualized lesions seen not to respond, or to only partially respond, can then be subjected to additional RF irradiation until the refractory lesion or lesions show the expected MR image response of dead tissue (image intensity enhancement and diminishing size over time).

The RF beads may be made from any materials that are sized to be able to be injected or inserted into the human body without causing harm. Associated with each RF bead would be electrical material that in response to RF energy at a given frequency would heat up. The bead may comprise nanoparticles or nanotubes. Most preferably, the beads would be bio-degradable such that once the treatment regiment is completed would pass through the subject. The beads also preferable should not interfere with the magnetic resonance imaging process so as to disturb the magnetic field.

The foregoing method may be done under the control of a computer or processor such that each of the above steps become coded instructions. For example, a computer may be programmed to use histogram data associated with the image from a site to determine whether treatment is complete, successful, partially successful, etc. For example, an histogram of the intensity within each voxel or pixel within an imaging volume may exhibit a trend as to how the image intensity enhancement associated with the site has changed in terms of absolute or relative image intensity. By monitoring these metrics, a program may then determine when to stop treatment, increase the energy of the beam, etc. In addition, by monitoring the size of the intensity histogram, the size of the tumor may be monitored over time.

Figure 18:
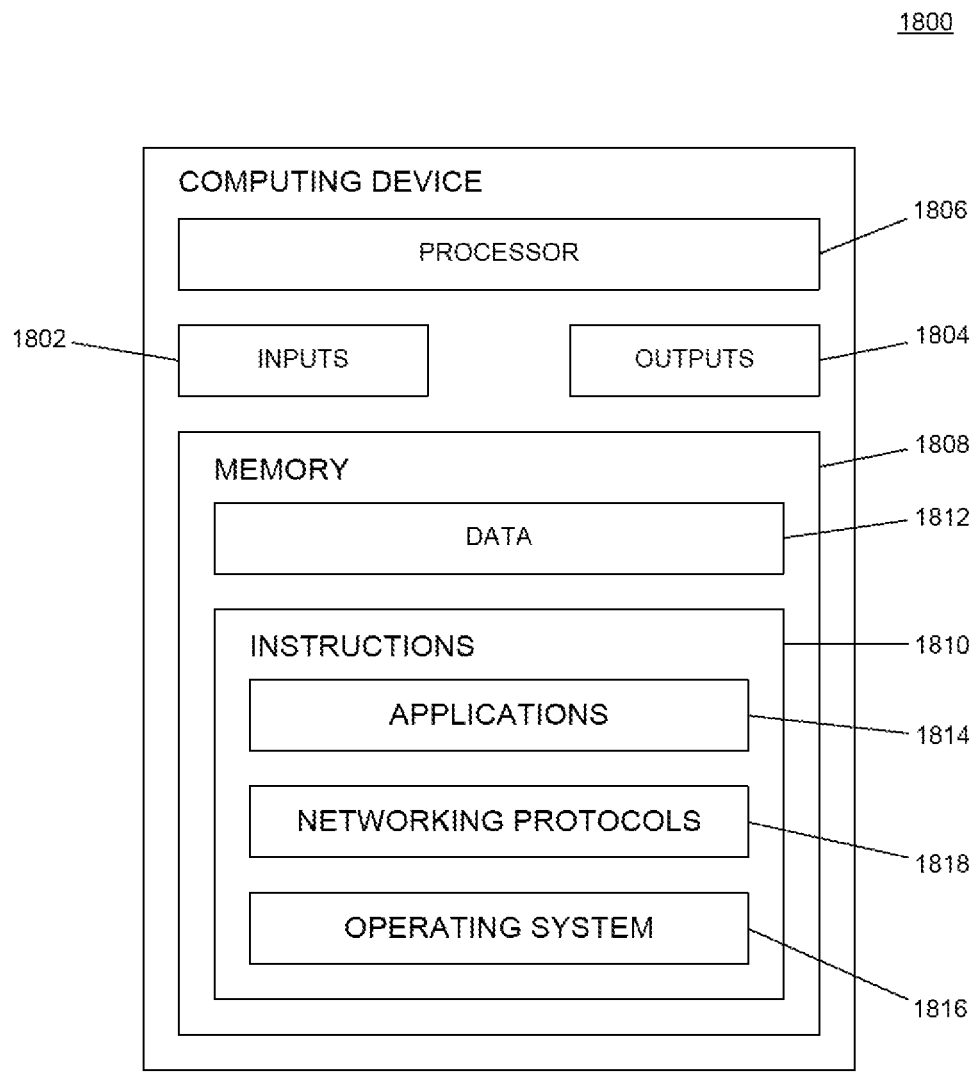
FIG. 18 illustrates a computer that may be programmed to perform the steps of FIG. 17 in accordance with a further aspect of the present invention.

A computer apparatus or device that may be used in accordance with the method is shown in FIG. 18. The apparatus 1800 may include, for example, one or more user inputs 1802 such as a keyboard and mouse and/or other types of input devices such as pen-inputs, joysticks, buttons, touch screens, etc., as well as a display 1804, which could include, for instance, a CRT, LCD, plasma screen monitor, TV, projector, etc. As shown, apparatus 1800 further contains a processor 1806, and memory or computer readable medium 1808.

Memory 1808 stores information accessible by the processor 1806, including instructions 1810 that may be executed by the processor 1808 and data 1812 that may be retrieved, manipulated or stored by the processor. The memory 1808 may be of any type capable of storing information accessible by the processor, such as a hard-drive, ROM, RAM, CD-ROM, DVD, Blu-Ray disk, flash memories, write-capable or read-only memories. The processor 1806 may comprise any number of well known processors, such as processors from Intel Corporation and Advanced Micro Devices. Alternatively, the processor 1806 may be a dedicated controller for executing operations, such as an ASIC.

The instructions 1810 may comprise any set of instructions to be executed directly (such as machine code) or indirectly (such as scripts) by the processor. In that regard, the terms "instructions," "applications" and "programs" are used interchangeably herein. The instructions may be stored in any computer language or format, such as in executable/object code or modules of source code. Generally, the instructions would form a set of machine executable instructions or source code that carry out steps 1716, 1726, 1730 and 1736 of FIG. 17.

Data 1812 may be retrieved, stored or modified by processor 1806 in accordance with the instructions 1810. The data may be stored as a collection of data. For instance, although the invention is not limited by any particular data structure, the data may be stored in computer registers, in a relational database as a table having a plurality of different fields and records, XML documents, or flat files.

The data may also be formatted in any computer readable format such as, but not limited to, binary values, ASCII etc. Similarly, the data may include images stored in a variety of formats. Moreover, the data may include any information sufficient to identify the relevant information, such as descriptive text, proprietary codes, pointers, references to data stored in other memories (including other locations in a network) or information which is used by a function to calculate the relevant data.

Data 1812 may include patient identification information. The patient identification information may be useful for properly identifying an image that is displayed on the display 1804 as an image of a particular patient, and may further be useful for verifying that the correct image is displayed. Data 1812 may also include histogram data collected from the MR images and threshold values that the computer uses to determine whether treatment is satisfactory or additional treatment is necessary to eradicate a particular site.

Although the processor 1806 and memory 1808 are functionally illustrated in FIG. 3 as being within the same block, it will be understood that the processor and memory may actually comprise multiple processors and memories that may or may not be stored within the same physical housing or location. For example, some or all of the instructions and data may be stored on a computer-readable removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 1808 such as hard drives, data centers, server farms or the like.

In addition, the memory 1808 in apparatus 1800 may include one or more applications or programs 1814 adapted to provide any of the functions described with respect to the computer 1800 and in accordance with the various aspects of the invention discussed above. Each device may include and execute specific instructions or applications, desirably under management of the processor 1806 in conjunction with an operating system 1816 and networking protocols instructions 1818 to provide the functionality described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for radio frequency ablation, comprising:
selectively transmitting radio frequency energy from a plurality of coils to two or more tuned radio frequency beads, each radio frequency bead located at a respective portion of anatomy of a subject and each radio frequency bead being tuned to a different resonant frequency; and
tuning a resonant frequency of the transmitted energy to selectively concentrate the energy so that each portion of the anatomy associated with a particular bead is heated,
wherein the plurality of coils comprise two or more nested coils and selectively transmitting comprises transmitting a main field of the radio frequency energy by a first one of the two or more nested coils and transmitting a focusing field by a second one of the two or more nested coils that focuses the main field.

2. The method of claim 1, further comprising selectively tuning the resonant frequency of the transmitted radio frequency energy so that each of the two or more tuned radio frequency beads is selectively heated.

3. The method of claim 2, further comprising elicting magnetic resonance image signals from at least one of the two or more portions of the anatomy at which the two or more beads are located.

4. The method of claim 3, further comprising providing a magnetic resonance image of at least one of the two or more portions of the anatomy at which the two or more beads are located using the elicited magnetic resonance image signals.

5. The method of claim 1, further comprising tuning the resonant frequency of the transmitted radio frequency energy so that each of the two or more tuned radio frequency beads is concurrently heated.

6. The method of claim 1, further comprising simultaneously monitoring each portion of the two or more portions of anatomy at which a tuned radio frequency bead is located using magnetic resonance imaging techniques.

7. The method of claim 1, further comprising concurrently monitoring each portion of the two or more portions of anatomy at which a tuned radio frequency bead is located using magnetic resonance imaging techniques.

8. The method of claim 7, further comprising repeating the transmitting and monitoring steps until the portion of the anatomy associated with a particular bead is determined to contain dead tissue.

9. The system of claim 1, wherein the respective portions of anatomy comprise different sites of the anatomy.

10. A radio frequency ablation system, comprising:
at least one radio frequency transmitter, the at least one radio frequency transmitter having a plurality of nested coils such that a first one of the plurality of nested coils generates a main field that is focused by a second one of the plurality of nested coils; and
two or more radio frequency beads, each bead is tuned to a different resonant radio frequency, and
wherein each of the two or more radio frequency beads is configured to be located at respective portions of an anatomy and the at least one radio frequency transmitter is configured to be selectively tuned to transmit energy at the resonant frequency of each of two or more radio frequency beads to selectively concentrate the energy in an area associated with the respective portions of the anatomy.

11. The system of claim 10, wherein a first bead of the two or more radio frequency beads is configured to be located at the first portion of the anatomy and a second bead of the two or more radio frequency beads is configured to be located at a second portion of the anatomy, the first and second beads being tuned to different radio frequencies.

12. The system of claim 11, wherein the at least one radio frequency transmitter is configured to transmit energy at each of the different frequencies of the first and second beads so as to selectively concentrate the energy at the first and second portions of the anatomy.

13. The system of claim 11, wherein the at least one radio frequency transmitter is configured to be selectively tuned to transmit energy at the resonant radio frequency of the first bead or the second bead.

14. The system of claim 11, wherein the at least one radio frequency transmitter is configured to be selectively tuned to concurrently transmit energy at each of the first and second resonant radio frequencies.

15. The system of claim 10 further comprising a magnetic resonance imaging system for eliciting magnetic resonance signals from the first portion of the anatomy.

16. The system of claim 15, further comprising a display that is configured to provide a visualization of an image associated with the magnetic resonance signals elicited from the first portion of anatomy.

17. The system of claim 10, wherein each bead comprises a resonant radio frequency circuit that is tuned to the respective different frequency.

18. The system of claim 17, where each bead includes the resonant radio frequency circuitry as a component.

19. The system of claim 10, wherein the respective portions of anatomy comprise different sites of the anatomy.

20. The system of claim 10, wherein the second coil is configured generates a field that is 180 degrees out of phase from the main field.

* * * * *